United States Patent
Davey et al.

[11] Patent Number: 5,725,471
[45] Date of Patent: Mar. 10, 1998

[54] MAGNETIC NERVE STIMULATOR FOR EXCITING PERIPHERAL NERVES

[75] Inventors: Kent R. Davey, New Smyrna Beach, Fla.; Charles Epstein, Atlanta, Ga.

[73] Assignee: Neotonus, Inc., Marietta, Ga.

[21] Appl. No.: 345,572

[22] Filed: Nov. 28, 1994

[51] Int. Cl.$^6$ ...................................................... A61N 1/00
[52] U.S. Cl. ............................................................ 600/13
[58] Field of Search ........................ 600/9–15; 607/48–52

[56] References Cited

U.S. PATENT DOCUMENTS

| | | | |
|---|---|---|---|
| 4,940,453 | 7/1990 | Cadwell | 600/15 |
| 5,066,272 | 11/1991 | Eaton et al. | 600/14 |
| 5,156,587 | 10/1992 | Montone | 600/13 |

FOREIGN PATENT DOCUMENTS

| | | | |
|---|---|---|---|
| 3930930 | 10/1990 | Germany | 600/13 |

OTHER PUBLICATIONS

K. Davey and Lanbo Luo, Toward Functional Magnetic Stimulation Theory (FMS) and Experiment, submitted to IEEE Transactions on Biomedical Engineering. (submitted in Jul. 1993).

K.R. Davey, et al., An Alloy–Core Electromagnet for Transcranial Brain Stimulation, J. Clin. Neurophysiol vol. 6, No. 4, p. 354.

C.M. Epstein et al., Localizing the Site of Magnetic Brain Stimulation in Humans, Neurology, vol. 40, pp. 666–670.

S.M.Hersch et al., Biological Consequence of Transcranial Magnetic Stimulation on the Mouse, Society for Neuroscience Abstracts, vol. 16, 551.7.

J.D. Weissman et al., Magnetic Brain Stimulation and Brain Size: Relevance to animal studies, vol. 85, pp. 215–219.

P.P.Brodak et al., Magnetic Stimulation of the Sacral Roots, Neuroourology and Urodynamics, vol. 12, pp. 533–540.

T. Kujirai et al., The Effect of Transcranial Magnetic Stimulation on Median Nerve Somatosensory Evoked Potentials, electroencephalography and clinical Neurophysiology, vol. 89, p. 227–234.

Y. Omura, et al. Basic Electrical Parameters for Safe and Effective Therapeutics . . . , Accupuncture and Electro–Therapeutics Res., Int., J., vol. 12, pp. 201–225.

R.W. Gulch and O. Lutz, Influence of Strong Static Magnetic Fields on Heart Muscle Contraction, Phys. Med. Biol., vol. 31, No. 7, pp. 763–767.

J. Bucking et al., The Influence of a Strong Magnetic Field on Muscular Contration, (Rad. ?) and Environ. Biophy., vol. 11, pp. 79–85.

"Mangetic Brain Stipulation and Brain Size: Relevance to Animal Studies," by J.D. Weissman, C.M. Epstein and K.R. Davey; Electroencephalography and clinical Neurophysiology 85 (1992) 215–219.

*Primary Examiner*—John P. Lacyk
*Attorney, Agent, or Firm*—Levisohn, Lerner, Berger & Langsam

[57] ABSTRACT

A magnetic nerve stimulator system is comprise of a core of highly saturable material with a coil winding. A thyrister capacitive discharge circuit pulses the device. A rapidly changing magnetic field is guided by the core, preferably vanadium permendur. For task specific excitation of various nerve groups, specially constructed cores allow for excitation of nerves at deeper levels with higher efficiency than is possible with air-core stimulators. Among the applications possible with this invention are treatment of incontinence, rehabilitation of large muscle groups in the leg and arm, and excitation of abdominal wall muscle groups to aid in weight loss and metabolic rate increase. A C-shape is employed for focussing the stimulation as desired.

44 Claims, 4 Drawing Sheets

MAGNETIC NERVE STIMULATOR FOR EXCITING PERIPHERAL NERVES

BACKGROUND OF THE INVENTION AND DESCRIPTION OF THE PRIOR ART

A nerve cell can be excited in a number of ways, but one direct method is to increase the electrical charge within the nerve, thus increasing the membrane potential inside the nerve with respect to the surrounding extracellular fluid. One class of devices that falls under the umbrella of Functional Electrical Stimulation (FES) realizes the excitation of the nerves by directly injecting charges into the nerves via electrodes which are either placed on the skin or in vivo next to the nerve group of interest. The electric fields necessary for the charge transfer are simply impressed via the wires of the electrodes.

FES is accomplished through a mechanism which involves a half-cell reaction. Electrons flow in wires and ions flow in the body. At the electro-electrolytic interface, a half-cell reaction occurs to accomplish the electron-ion interchange. Unless this half-cell reaction is maintained in the reversible regime, necrosis will result—partially because of the oxidation of the half-cell reaction and partially because of the chemical imbalance accompanied by it.

The advantage of FES is that the stimulation can usually be accomplished from extremely small electrodes with very modest current and voltage levels. The disadvantage however, is that it involves half-cell reactions. Most rehabilitation programs using FES place the electrodes directly on the skin. A conductive gel or buffering solution must be in place between the electrodes and the skin surface. Long term excitation of nerve or muscle tissue is often accompanied by skin irritation due to the current concentration at the electrode/skin interface. This problem is especially aggravated when larger excitation levels are required for more complete stimulation or recruitment of the nerve group.

By contrast, magnetic stimulation realizes the electric fields necessary for the charge transfer by induction. Rapidly changing magnetic fields induce electric fields in the biological tissue; when properly oriented, and when the proper magnitude is achieved, the magnetically induced electric field accomplishes the same result as realized by FES, that of transferring charge directly into the nerve to be excited. When the localized membrane potential inside the nerve rises with respect to its normal negative ambient level of approximately −90 millivolts (this level being sensitive to the type of nerve and local pH of the surrounding tissue), the nerve "fires."

The present invention is especially targeted at applications that are not suited for the use of implanted electrodes. The invention is preferred for use in those situations where stimulation can be achieved noninvasively. In those applications which include incontinence and rehabilitation of muscle groups as well as potential weight loss treatment, the desired excitation levels using FES often fall outside of what might be considered comfortable limits. That is, the electrical current that ideally would be injected through the skin to excite the muscle groups of interest often leads to some skin irritation with time. Even in applications where this is not the case, the mandatory use of gels and direct electrode/skin placement is inconvenient and is often resisted by the patient.

Magnetic excitation, on the other hand, has the attractive feature of not requiring electrode skin contact. Thus, stimulation can be achieved through the clothing that is being worn. This overcomes the objection of inconvenience and preservation of a patient's dignity. Secondly, because there is no direct contact, stronger excitation levels can be realized without undue additional skin irritation. A contribution offered by the present invention is the ability to achieve higher levels of focusing of the magnetic field and thus stimulation within the patient. Commensurate with this greater level of focusing comes some flexibility in the number of possible applications that might be targeted. Also accompanying the higher degree of focus is a higher level of power efficiency. Typically, the devices being designed by the methods outlined in this invention reduce the magnetic reluctance path by a factor of two. This reluctance reduction translates into a diminution of the current by the same factor and a fourfold reduction in power loss.

Magnetic stimulation of neurons has been heavily investigated over the last decade. Almost all magnetic stimulation work has been done in vivo. The bulk of-the magnetic stimulation work has been in the area of brain stimulation. Cohen has been a rather large contributor to this field of research (See e.g., T. Kujirai, M. Sato, J. Rothwell, and L. G. Cohen, "The Effects of Transcranial Magnetic Stimulation on Median Nerve Somatosensory Evoked Potentials", *Journal of Clinical Neurophysiology and Electro Encephalography*, Vol. 89, No. 4, 1993, pps. 227–234.) This work has been accompanied by various other research efforts including that of Davey, et al. (See, K. R. Davey, C. H. Cheng, C. M. Epstein "An Alloy—Core Electromagnet for Transcranial Brain Stimulation", *Journal of Clinical Neurophysiology*, Volume 6, Number 4, 1989, p.354); and that of Epstein, et al. (See, Charles Epstein, Daniel Schwartzberg, Kent Davey, and David Sudderth, "Localizing the Site of Magnetic Brain Stimulation in Humans", *Neurology*, Volume 40, April 1990, pps. 666–670). The bulk of all magnetic stimulation research attempts to fire nerves in the central nervous system.

The present invention differs in a number of respects from previous research and efforts. First, the present invention has primary applicability to the peripheral nervous system, although it can be employed to stimulate nerves in the central nervous system as well. Second, and more importantly, the previous nerve stimulation work is dominated almost exclusively by air core coils of various shapes and sizes. The present invention, as will be discussed, relates to the use of a core of a highly saturable material, preferably vanadium permendur. Among the air core stimulators are circles, ovals, figure eights, and D shaped coils. The coils are normally excited by a capacitive discharge into the winding of the core of these coils. This exponentially decaying field has a time constant typically in the neighborhood of 100 microseconds. Typical target values for the magnetic field peak happen to be near two Tesla. J. A. Cadwell is perhaps the leader among those who are now using and marketing these air core stimulators. Among his primary patents is U.S. Pat. No. 4,940,453 entitled "Method and Apparatus for Magnetically Stimulating Neurons" Jul. 10, 1990. There are a number of power supplies all of which operate on a basic capacitive type discharge into a number of air core coils which are sold with his units. Various shaped coils are being explored at this time. One such coil is a cap shaped device which fits over the motor cortex (K. Krus, L. Gugino, W. Levy, J. Cadwell, and B. Roth "The use of a cap shaped coil for transcranial stimulation of the motor cortex", *Journal of Neurophysiology*, Volume 10, Number 3, 1993, pages 353–362).

Some efforts are being given to various circuits used to fire these air core coils. H. Eton and R. Fisher offer one such alternative in their patent "Magnetic Nerve Stimulator" U.S. Pat. No. 5,066,272 Nov. 19, 1991. They suggest the use of two capacitors—one to capacitively discharge into the coil of interest, and a second to recover the charge from the inductive energy resident in the coil. The circuit used in the present invention accomplishes the same objective with a single capacitor.

Some stimulation research is being performed on the peripheral nervous system (See e.g., Paul Maccabee, V. Amassian, L. Eberle, and R. Cracco, "Magnetic Coil Stimulation of Straight and Bent Amphibian and Mammalian Peripheral Nerve in vitro: Locus of Excitation, " *Journal of Physiology*, Volume 460, Januar 1993, pages 201–219.) The bulk of Maccabee's work is however targeted for cranial excitation. The applications of the present invention focus on the peripheral nervous system although it can be used on the central nervous system, as well.

SUMMARY OF THE INVENTION

Magnetic stimulation of peripheral nerves has the advantages of convenience and threshold variability over competing FES systems. An advance of the present invention over competing magnetic nerve stimulators is in the. use of a magnetic core of highly saturable material, and in the design of the magnetic core stimulator itself.

An objective of the present invention is to "fire" a coil having about a 100 microsecond characteristic decay time, fifteen times per second. The system must be reasonably efficient and reliable to fire at such a high repetition rate. This rate is necessary to keep the muscle groups more or less continuously stimulated.

The exact stimulation frequency will be varied somewhat depending on the requirements of the application. Sometimes muscle groups will need to be excited for a five second period, followed by rest for a five second period and then be stimulated continuously for another five seconds and then rest again. While they are being stimulated, it is desirable to have the muscle groups continuously excited. This requirement dictates the necessity of continuing to pulse the cores at a repetition rate of 15 Hz. Because of the large currents involved during any given firing of the core, it is necessary to make the cores as efficient as possible. It is desirable to focus the magnetic field into the region targeted for stimulus to the exclusion of surrounding regions. The specially designed cores offered by this invention realize that focusability, whereas the air core coils used by the prior art do not.

The simplest core that might be selected would be that of a "C" shaped core. The span of the "C" must be carefully chosen; the span affects both the penetration depth and the magnitude of the field. Possibly of more importance is the construction of the core. The best cores are constructed from thin laminate, highly saturable material. A typical core might be wound using two mil stock of vanadium permendur. A long ribbon of such material is wound on a mandrel (e.g. a mandrel of wood or plastic) for the radius, thickness and depth desired. Each side of the ribbon is coated with a thin insulative coating to electrically isolate it from its neighbor. A generic core that might be used at various locations around the body might span an angle of about 210°. Once the ribbon has been wound on the mandrel to the desired dimensions, it is dipped in epoxy to freeze its position. Once the epoxy has dried, the mandrel is removed and the core may be cut for the span of angle desired. The cut may destroy the electrical isolation of adjacent laminations. Each cut must be finely ground so that it is smooth, and then a deep etch performed. The deep etch is performed by dipping each of the cut ends in an acid bath. This causes the cut ends to delaminate slightly, but maintains the electrical isolation of the laminations. Failure to perform this deep etch seems to result in considerable eddy current loss and heating at the cut ends of the core. Following the deep etch, the ends are brushed with epoxy to maintain the shape and structural integrity of the core. The final step of the construction is to wind a coil of insulated wire about the core. A typical inductance for a core of this type is about 20 μH. The present invention, however, may be practiced at other inductances or magnetic field strengths, as well.

In the simplest configuration, each core has only one winding. The winding is excited by an exponentially decaying pulse with a characteristic time of about 20 μs. The actual signal has a ringing period of about that time within an envelope that is exponentially decaying so that only two to three cycles are ever witnessed by the coil current. The excitation is repeated on a period of about 15–20 Hz. As stated above, the repetition cycle of these patterns will be varied according to the application. The circuit usually consists of a transformer which feeds into a full wave rectifier bridge. The bridge voltage charges the capacitor; the charge on the capacitor is triggered with a silicon control rectifier to drive current into the coil. The return charge coming back through the coil the second time is fed through the diode back into the capacitor to prepare the circuit for the second phase of excitation.

There are three principal target applications for this invention—incontinence, muscle rehabilitation, and weight control treatment. For the treatment of incontinence, it is necessary to stimulate the pelvic floor muscles. Such a stimulation is achieved by concentrating and focusing magnetic flux directly up the vaginal cavity. One suitable core capable of realizing this objective is constructed by combining two individual "C" cores each spanning an angle of about 210°. The legs of the cores are brought together in a central region. The common central leg of the two "C" cores is wound by a coil and the return path for the flux is split between the two "C"s. The cores themselves fit proximally and distally on a saddle upon which the patient sits during treatment.

The second area of potential application is in the rehabilitation of muscles. The primary muscle groups targeted are the thigh, calf, biceps, and triceps. The geometry is similar for all these applications, and thus a cylindrical extension around the muscle is used. Although one solution for this problem is a simple "C" core and coil which is moved around by the discretion of the patient, a more suitable stimulator resembles the tubular shape motors used in electromechanics to propel a secondary member down a tube. Here the geometry would necessarily require a hinged tubular shape having recesses or slots which would run azimuthally around the muscle group to be stimulated. The coils of the stimulator fits in these recesses or slots and the surrounding structure would again be a laminated vanadium composite. If the structure were fitted with two or three coils, they could be stimulated in a phased arrangement.

Such an excitation would have the effect of kneading the muscle tissue group along its longitudinal axis. This particular excitation pattern may be instrumental in more fully recruiting larger muscle groups such as the hamstring group in the leg. Full recruitment or stimulation of the nerve group would be advantageous to long term rehabilitation. Preliminary experiments with the device indicate that excitations at the frequencies mentioned accomplish exercise of the muscles at a higher efficiency and rate than could be accomplished through normal means.

Another area of potential application is that of assisting in weight loss management. As with muscle rehabilitation, one alternative is to simply use a handheld unit moved over multiple areas of the body. One particularly difficult group to stimulate might be the abdominal wall. A possible method for realizing excitation of this group would resemble a chest plate that might be hinged to the side of a chair in which the patient sits. The chest plate would contain a two or three phase arrangement of coils backed by the laminated vanadium cores constructed in the manner dictated above. The cores would be spaced to drive the flux deeply within the abdominal muscle group. Both in muscle rehabilitation and in weight loss management, the phasing of the coils can be alternated with time to give the effect of a back and forth "kneading" stimulation pattern. The rationale behind weight management is that the firing of these muscle groups requires the uptake of adenosine triphosphate; this energy expenditure is being artificially induced by the magnetic stimulator.

In summary, it is noted that there are a number of ways to more efficiently stimulate various muscle groups within the body. The key to these more efficient techniques revolves around using high saturation thin laminate material to construct these cores and thereby drive and focus the flux into the regions desired. A simple "C" type core achieves a reluctance advantage of at least a factor of two over conventional cores. By using multiple cores connected at a center leg, a single focus site can be achieved with the return path disbursed in two or more areas so as to discourage excitation when the field is returned. In other applications, multiphased coils that actually enclose the tissue of interest can be excited so as to roll or knead muscle groups directionally with time. Certain wrapping applications may be more instrumental for higher recruitment of injured muscle groups.

DETAILED DESCRIPTION OF THE INVENTION AND THE PREFERRED EMBODIMENT

Figure 1:
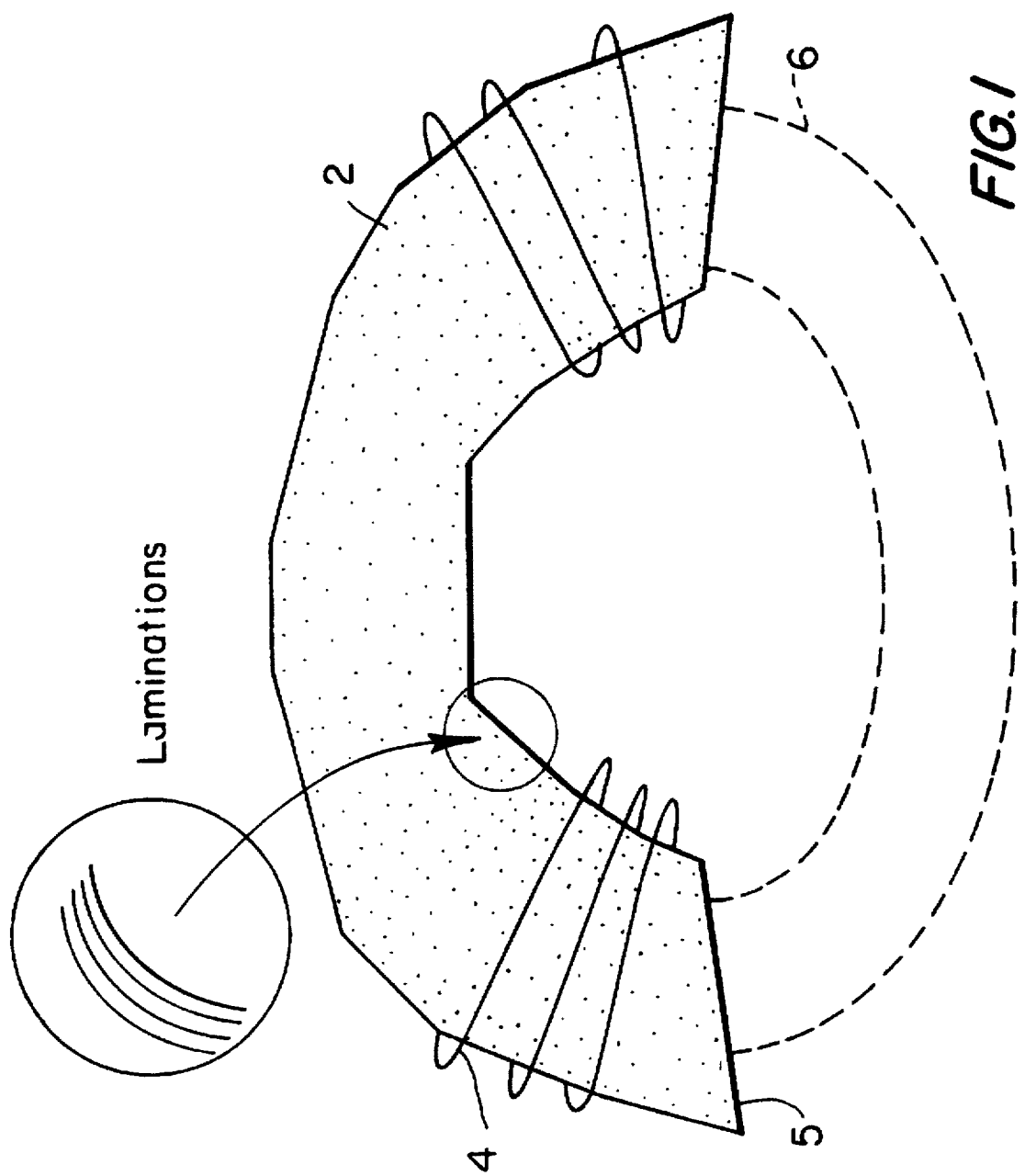
FIG. 1 is a plan view of a "C" shaped core stimulator with the toroidal coil field winding wrapped around the core. The field lines (dotted) indicate the depth of penetration and focusing of the stimulation.

As shown in FIG. 1, a "C" shaped core is capable of stimulating various peripheral nerve groups throughout the body. The core 2 is constructed by winding two to four mil laminations of a highly saturable material on a mandrel; the number of laminations required will be dictated by the thickness and depth of the core desired. This closed loop spool of laminations is removed from the mandrel and coated with epoxy to give the unit structural integrity. The closed loop is then cut to give the length and angle of the "C" shape, as desired. A deep acid etch is then performed on the cut edges. The cut edges are soaked in an acid bath which causes the epoxy to dissolve resulting in a slight delamination of the core in the vicinity of the cut. Epoxy is then brushed on the etched ends to prevent further delamination. This procedure is necessary to prevent eddy currents from flowing in the core. This would diminish the effective B field which can be produced by the core. The characteristic magnetic fields in the cores have strengths in the range of two Tesla. The laminate material must be constructed of a highly saturable material. Preferably, vanadium permendur is used. This material carries a high field density. In this application, high saturation is more important than high permeability. A winding or coil 4 is then wrapped around the core in such a way as to drive the flux through the cut ends 5. The field lines 6 give an indication of the depth of penetration and degree of focusing expected with such a core.

Figure 2:
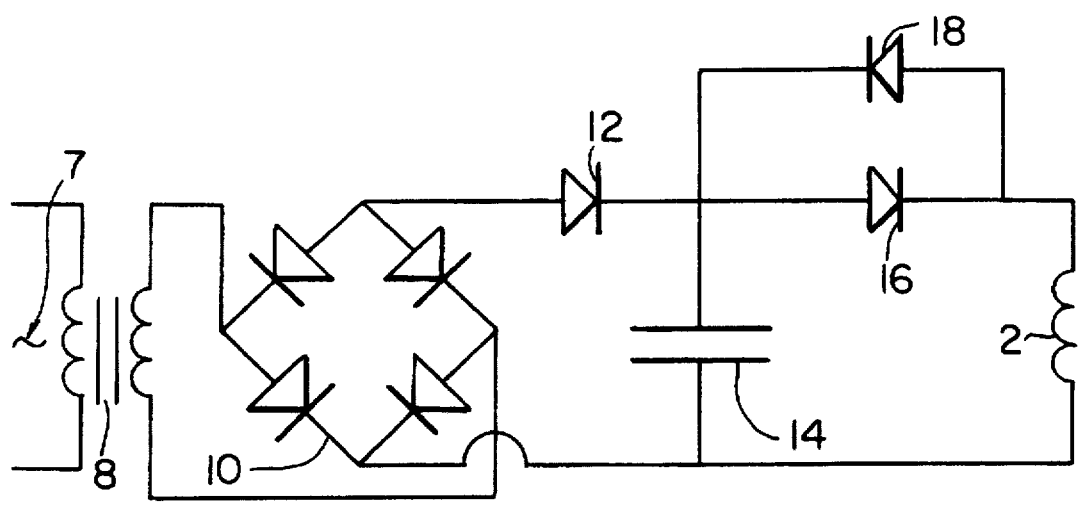
FIG. 2 is a schematic of the electrical circuit used to stimulate the coil winding.

FIG. 2 shows an electrical circuit used to "fire" the core and coil of FIG. 1. A normal 120 volt, 60 Hz signal excites the circuit at 7. A transformer 8 amplifies the voltage up to about 1–3 kV. This high voltage AC signal is then fed into a full wave rectifier bridge 10. The signal from the rectifier bridge is then passed through a diode 12 to charge a capacitor 14. The purpose of all the electrical components to the left or upstream of the capacitor is to simply put charge into the capacitor: The energy residing in the circuit which will be pumped into the stimulator core is one-half C (the capacitance value) times the voltage squared. When thyrister 16 is triggered with a small control voltage pulse, current flows through the thyrister and into the core 2. Most of this energy goes back into the capacitor 14, recharging it in the opposite polarity from its initial charge. The reverse charged capacitor 14 immediately discharges again through the stimulator coil 2 through diode 18, connected in parallel. Theoretically, all of this energy should pass into capacitor 14 to recharge it according to its initial polarity. In practice, of course, this LC circuit has some loss, and the thyrister 16 does not shutoff immediately. Two to three exponentially decaying ring cycles of this L circuit are witnessed in practice before current of core 2 is completely shut off. After shutoff, the capacitor charges through diode 12 as it did initially. It continues to charge until thyrister 16 is triggered again.

Different stimulation/rest cycles are employed for different tasks. In the treatment of incontinence, one such stimulation cycle might be five seconds on, five seconds off. During the five seconds which are characterized as "on", thyrister 16 would continuously be pulsed 15 times per second. These stimulation montages can be altered according to the requirements and goal of the stimulation protocol.

The circuit shown is a preferred embodiment for the practice of this invention but other circuit designs (such as a dual capacitor arrangement or so forth) may be used to fire the coil as well, as will be apparent to those skilled in the art. Moreover, whereas the magnetic field produced by this embodiment pulses at approximately 20–50 kHz, variations in that frequency may be practiced as well.

Figure 3:
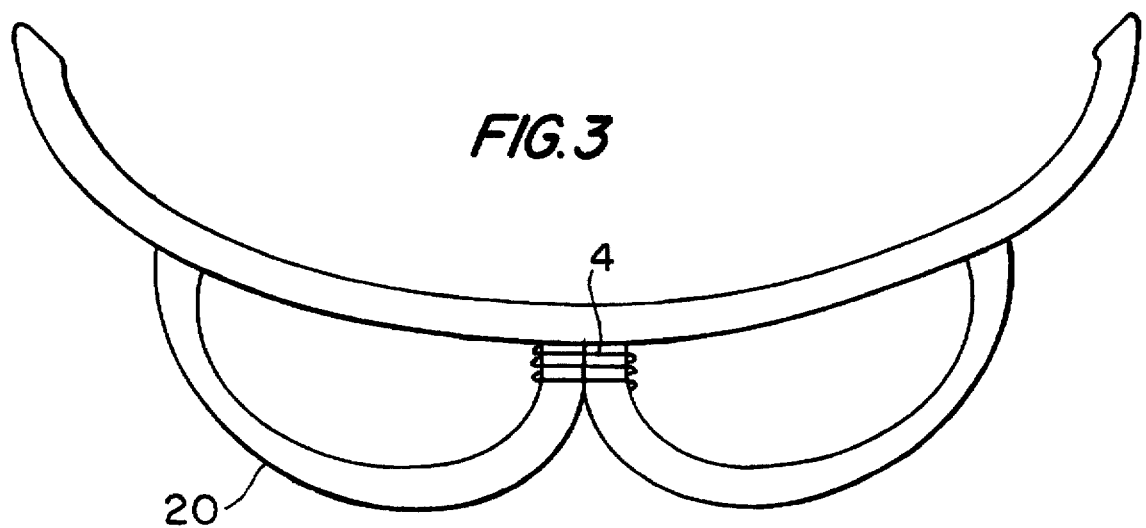
FIG. 3 is a top plan view of a core stimulator configuration used in the treatment of incontinence; the core is designed to fit underneath a saddle shaped cushion in which the patient sits during treatments.

Shown in FIG. 3 is a dual "C" core type arrangement suitable for the treatment of incontinence. The individual "C"s comprising this core each span an angle of about 220°. The cores 20 are placed end to end in a W type arrangement. The winding 4 is wrapped around the common center leg of the two cores. The cut ends of these cores are designed to be flush with the lower side of a saddle cushion 21 in which the patient sits. The primary flux is driven up the common central core into the vaginal cavity. This flux is returned through the posterior and anterior arms of the "W". Because the return flux is much lower in magnitude, no stimulation occurs except at the vaginal floor near the center leg of the "W".

Figure 4:
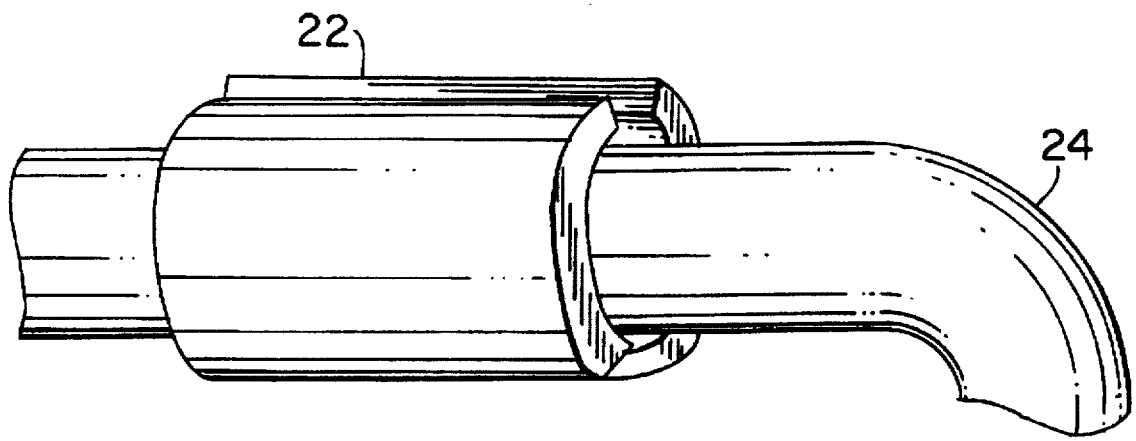
FIG. 4 is a perspective view of a core stimulator (wrapped around a patient's leg) used to massage muscles in the leg for rehabilitation purposes. The tubular core is hinged on one side and is designed to fold around the leg.
Figure 5:
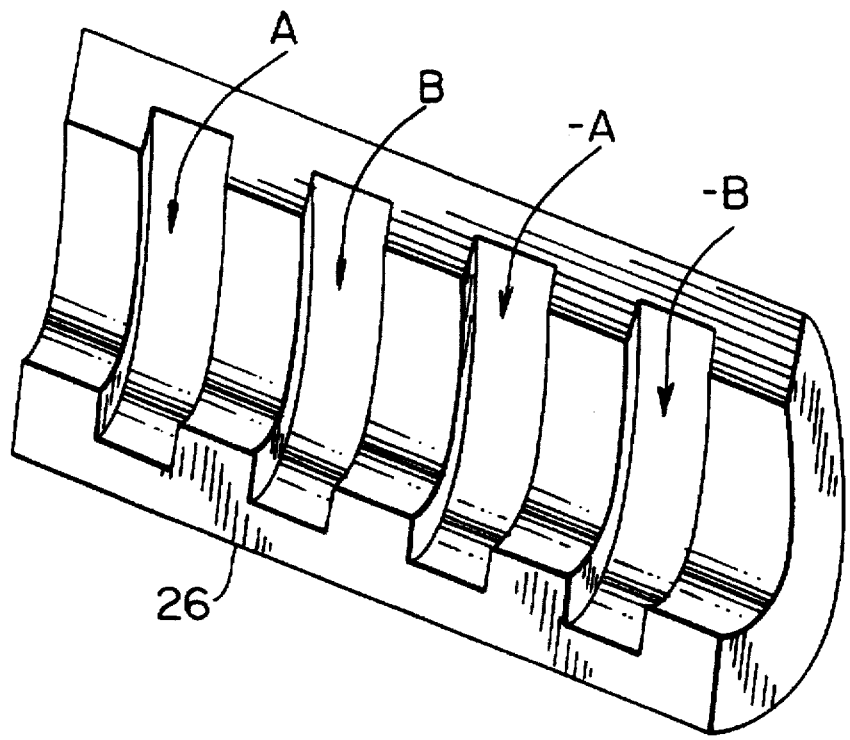
FIG. 5 is a perspective view of a half section of the core stimulator used for arm or leg muscle rehabilitation; windings of different phases are placed in adjacent recesses or slots, cut into the core.
Figure 6:
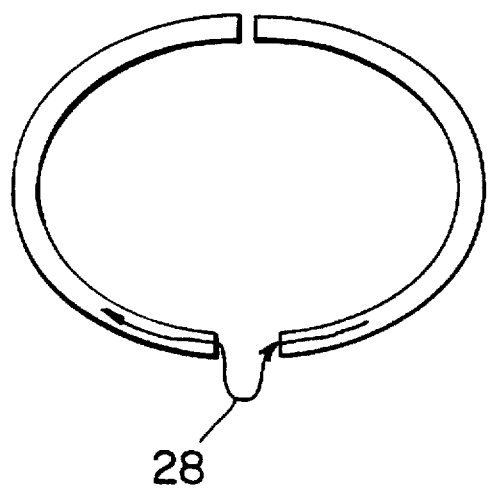
FIG. 6 is an end view of the leg or arm stimulator. The winding going from one section to the next is taken out in a long fold to allow for ease of opening of the core units for facilitating placement around the leg or arm.

FIG. 4 shows a core stimulator suitable for exciting leg and arm muscle groups. In this configuration the cores 22 would constitute a tubular type shroud into which a leg 24 or an arm would be inserted. Although the "C" core of FIG. 1 would be suitable for this task, its geometry is difficult to achieve a homogenous and controlled stimulus of this muscle group. As shown in FIG. 5, each section of the stimulator 22 is comprised of two half shells 26. Recesses or slots 27 are cut into the half shells to allow placement of coils which will be wound preferentially within the shells. The individual windings of the shell 26 are aligned in such a way as to create a magnetic field which is preferentially along the axis of the arm or the leg. Adjacent recesses or slots of the stimulator 22 will contain different phases. A two or three phase arrangement is used to excite a traveling magnetic field which moves down and up the axis of the arm/leg. This winding arrangement is not unlike that used in tubular motors to realize an axial traveling wave. One edge of the two common halves constituting the stimulator 22 must act as a hinge. The winding electrically connecting the two halves is simply accomplished by bringing the wire down as an extension 28 as suggested in FIG. 6. The extra length of winding associated with the extension 28 guarantees the needed flexibility of the stimulator to hinge and wrap around the patient's arm or leg.

Figure 7:
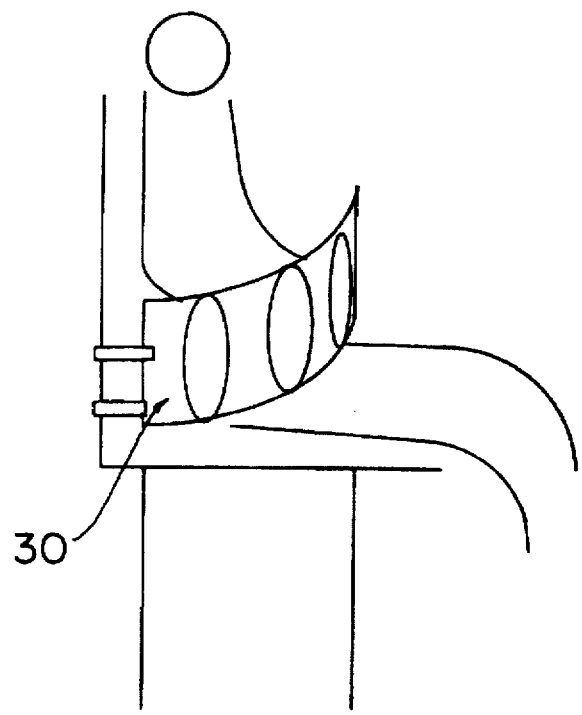
FIG. 7 is a schematic perspective view of a hinged multiphased stimulator designed to conform around the torso of the patient.

FIG. 7 suggests yet another alternative embodiment suitable for the stimulation of abdominal muscles. Here the stimulator 30 is hinged to a chair into which the patient sits. The stimulator then folds around the patient's abdomen during treatment. The stimulator 30 is again constructed of laminated highly permeable, highly saturable material. Multiple windings are laid in recesses or slots which are cut into the core. The windings are designed to drive flux into the abdomen and cause a contraction of the abdominal wall muscle group. Again the windings can be phased to cause a directional massaging of this muscle group.

Having described this invention with regard to certain specific embodiments, it is to be understood that the description is not meant as a limitation since further modifications may now suggest themselves to those skilled in the art and it is intended to cover such modifications as fall within the scope of the appended claims.

I claim:

1. A magnetic nerve stimulator comprising:
   (a) an arc shaped core spanning an angle of less than three hundred sixty degrees (360°), said arc shaped core comprising vanadium permendur;
   (b) a stimulator coil, said coil at least partially wrapped around said core; and
   (c) electric current means connected to said stimulator coil to create a current flow in said stimulator coil that causes said stimulator coil and said core to generate a magnetic field.

2. A magnetic nerve stimulator as claimed in claim 1, wherein said arc shaped core spans an angle of approximately 210 degrees thereby defining an opening of approximately 150 degrees, wherein said magnetic field is focussed beyond said opening.

3. A magnetic nerve stimulator as claimed in claim 1, wherein said core is approximately C shaped.

4. A magnetic nerve stimulator as claimed in claim 1, wherein the shape of said core focuses and/or concentrates the magnetic field produced by said coil and said core.

5. A magnetic nerve stimulator as claimed in claim 1 wherein said core is substantially tubular.

6. A magnetic nerve stimulator as claimed in claim 5, wherein said core comprises at least one recess for holding said coil.

7. A magnetic nerve stimulator as claimed in claim 1 wherein said electric current means comprises:
   (a) a power supply;
   (b) a transformer connected to said power supply;
   (c) a full wave rectifier bridge connected to said transformer;
   (d) a diode connected to said full wave rectifier bridge;
   (e) capacitor means connected to said diode;
   (f) a thyristor connected to said capacitor means, said thyristor connected to said stimulator coil; and
   (g) a second diode connected to said capacitor means, said second diode also being connected to said stimulator coil.

8. A magnetic nerve stimulator as claimed in claim 7, wherein said capacitor means comprises a single capacitor.

9. A magnetic nerve stimulator as claimed in claim 1, wherein the decay time of said coil is about one hundred (100) microseconds.

10. A magnetic nerve stimulator as claimed in claim 1, wherein said coil generates a magnetic field at least about fifteen (15) times per second.

11. A magnetic nerve stimulator as claimed in claim 1, wherein said core defines an arc of approximately two hundred ten (210) degrees.

12. A magnetic nerve stimulator as claimed in claim 1, wherein said core comprises a ribbon of said saturable material coated with a thin insulative coating.

13. A magnetic nerve stimulator as claimed in claim 12, wherein said ribbon is further provided with an epoxy coating.

14. A magnetic nerve stimulator as claimed in claim 3, wherein the ends of said core are smoothly ground.

15. A magnetic nerve stimulator as claimed in claim 1, further comprising at least two approximately C shaped cores, said two C-shaped cores being held closely together to form a common leg, and wherein said coil is wrapped around a portion of said common leg.

16. A magnetic nerve stimulator as claimed in claim 1, wherein two of said cores are provided, said cores being C-shaped, and wherein said magnetic nerve stimulator further comprises a seat for a user to sit upon, said cores being located underneath said seat yet the magnetic field produced by said magnetic nerve stimulator being above said seat.

17. A magnetic nerve stimulator as claimed in claim 16, wherein said cores produce a magnetic field during operation of said stimulator, said magnetic field being focused in the direction of a user's bladder muscles when the user sits on said seat.

18. A magnetic nerve stimulator as claimed in claim 1, where said stimulator comprises at least a section which wraps around a portion of a patient's abdomen.

19. A method for magnetically stimulating the nerves of an organism comprising the steps of:
   (a) charging a capacitor with an electric charge;
   (b) discharging said capacitor through a stimulator coil, said stimulator coil at least partially surrounding a core comprising vanadium permendur; and
   (c) stimulating the nerves of said organism using the magnetic field generated by said stimulator coil and said core.

20. A method as in claim 19, wherein said highly saturable material comprises vanadium permendur.

21. A method as in claim 19, wherein said nerves are part of the peripheral nervous system of said organism.

22. A method as in claim 19, further comprising the step of stimulating said nerves for the treatment of incontinence.

23. A method as in claim 19, further comprising the step of stimulating said nerves for the purpose of weight control.

24. A method as in claim 19, further comprising the step of stimulating said nerves for the purpose of muscle rehabilitation.

25. A method as in claim 19, further comprising the step of stimulating said nerves in cycles, said cycles comprising periods of stimulation of said nerves and periods of rest of said nerves.

26. A method as in claim 19, further comprising the step of focusing and/or concentrating said magnetic field into a desired region.

27. A magnetic nerve stimulator comprising:
(a) a core of highly saturable material;
(b) a stimulator coil, said coil having its longitudinal axis located within the geometric outer boundaries defined by said core; and
(c) electric current means connected to said stimulator coil to create a current flow in said stimulator coil that causes said stimulator coil and said core to generate a magnetic field, said electric current means comprising:
  (i) a power supply;
  (ii) a transformer connected to said power supply;
  (iii) a full wave rectifier bridge connected to said transformer;
  (iv) a diode connected to said full wave rectifier bridge;
  (v) capacitor means connected to said diode;
  (vi) a thyristor connected to said capacitor means, said thyristor connected to said stimulator coil; and
  (vii) a second diode connected to said capacitor means, said second diode also being connected to said stimulator coil.

28. A magnetic nerve stimulator as claimed in claim 27, wherein said highly saturable material is a material capable of maintaining a magnetic field of approximately two (2) Tesla within said core.

29. A magnetic nerve stimulator as claimed in claim 27, wherein said core comprised vanadium permendur.

30. A magnetic nerve stimulator as claimed in claim 27, wherein said core defines an arc of approximately two hundred ten (210) degrees.

31. A magnetic nerve stimulator as claimed in claim 30, wherein said highly saturable material comprises vanadium permendur.

32. A magnetic nerve stimulator comprising:
(a) an arc shaped core spanning an angle of approximately two hundred ten (210) degrees and having an opening of approximately one hundred fifty (150) degrees, said core comprising a highly saturable material;
(b) a stimulator coil wrapped around at least a portion of said core; and,
(c) electric current means connected to said stimulator coil to create a current flow in said stimulator coil that causes said stimulator coil and said core to generate a magnetic field, said magnetic field being focussed beyond said opening.

33. A magnetic nerve stimulator as claimed in claim 32, wherein said highly saturable material is a material capable of maintaining a magnetic field of approximately two (2) Tesla within said core.

34. A magnetic nerve stimulator as claimed in claim 32, wherein said highly saturable material comprises vanadium permendur.

35. A magnetic nerve stimulator comprising:
(a) a seat for a user;
(b) two C-shaped cores in proximity to one another to form a common leg portion, said cores comprising highly saturable material and located beneath said seat;
(c) a stimulator coil wrapped around at least a portion of said cores, including said common leg portion; and,
(d) electric current means connected to said stimulator coil to create a current flow in said stimulator coil that causes said stimulator coil and said cores to generate a magnetic field.

36. A magnetic nerve stimulator as claimed in claim 35, wherein said highly saturable material is a material capable of maintaining a magnetic field of approximately two (2) Tesla within said core.

37. An apparatus as claimed in claim 35, wherein said electric current means comprises:
  (i) a power supply;
  (ii) a transformer connected to said power supply;
  (iii) a full wave rectifier bridge connected to said transformer;
  (iv) a diode connected to said full wave rectifier bridge;
  (v) capacitor means connected to said diode;
  (vi) a thyristor connected to said capacitor means, said thyristor connected to said stimulator coil; and
  (vii) a second diode connected to said capacitor means, said second diode also being connected to said stimulator coil.

38. An apparatus as claimed in claim 37, wherein each of said C-shaped cores comprise vanadium permendur and comprise an angle of approximately 220 degrees.

39. An apparatus as claimed in claim 35, wherein each of said C-shaped cores comprise an angle of approximately 220 degrees.

40. An apparatus as claimed in claim 39, wherein said cores comprise vanadium permendur.

41. A method for treating incontinence in an organism by magnetically stimulating the nerves of the organism, comprising the steps of:
(a) providing a magnetic nerve stimulator, said stimulator comprising at least one core of highly saturable material, and a stimulator coil at least partially surrounding said core;
(b) passing an electric current through said coil to generate a magnetic field; and,
(c) treating incontinence in said organism by stimulating the nerves of said organism using said magnetic field.

42. A magnetic nerve stimulator as claimed in claim 41, wherein said highly saturable material is a material capable of maintaining a magnetic field of approximately two (2) Tesla within said core.

43. A method as claimed in claim 41, wherein said core comprises an angle of approximately two hundred and ten (210) degrees, with an opening of approximately one hundred and fifty (150) degrees.

44. A method as claimed in claim 43, wherein said highly saturable material comprises vanadium permendur.

* * * * *